US008808003B2

(12) United States Patent
Northcutt (10) Patent No.: US 8,808,003 B2
(45) Date of Patent: Aug. 19, 2014

(54) LUNCH BOX BOARD GAME (75) Inventor: Elizabeth Lynn Northcutt, Lago Vista, TX (US)

(73) Assignee: Elizabeth Lynn Northcutt, Lago Vista, TX (US)

( * ) Notice: Subject to any disclaimer, the term of this patent is extended or adjusted under 35 U.S.C. 154(b) by 124 days.

(21) Appl. No.: 13/396,117

(22) Filed: Feb. 14, 2012

(65) Prior Publication Data

US 2012/0237905 A1  Sep. 20, 2012

Related U.S. Application Data

(60) Provisional application No. 61/442,446, filed on Feb. 14, 2011.

(51) Int. Cl.
*G09B 19/22* (2006.01)
*G09B 19/00* (2006.01)
*A63F 9/18* (2006.01)
*A63F 3/04* (2006.01)
*A63F 3/00* (2006.01)
*A63F 1/04* (2006.01)

(52) U.S. Cl.
CPC ............... *A63F 3/00006* (2013.01); *A63F 9/18* (2013.01); *A63F 2003/0486* (2013.01); *G09B 19/0092* (2013.01); *A63F 2003/00018* (2013.01); *A63F 2001/0408* (2013.01)
USPC .......................................................... 434/129

(58) Field of Classification Search
USPC ................. 434/127, 128, 129, 236, 237, 247; 273/242, 243, 302
See application file for complete search history.

(56) References Cited

U.S. PATENT DOCUMENTS

| 4,986,757 | A | 1/1991 | Mueller |
|---|---|---|---|
| 5,062,645 | A | 11/1991 | Goodman et al. |
| 5,215,309 | A | 6/1993 | Joel |
| 5,544,891 | A | 8/1996 | Gibson et al. |
| 5,704,611 | A | 1/1998 | Pierce |
| 5,897,115 | A | 4/1999 | Sherry et al. |
| 5,931,469 | A | 8/1999 | Stichnoth |
| 5,988,642 | A | 11/1999 | Ziemba et al. |
| 6,019,370 | A | 2/2000 | Morris |
| 6,120,028 | A | 9/2000 | Boyer |
| 6,454,263 | B1 | 9/2002 | Bandieri |
| 7,234,699 | B2 | 6/2007 | Putnam |
| 7,494,127 | B2 * | 2/2009 | Schmidt ........................ 273/299 |
| 7,568,700 | B2 | 8/2009 | Bentley |
| 7,798,493 | B1 | 9/2010 | Moore |
| 7,806,406 | B1 | 10/2010 | Simikic |
| 7,832,730 | B2 | 11/2010 | Calderon |
| 7,887,057 | B1 | 2/2011 | Brodie et al. |

(Continued)

*Primary Examiner* — Kurt Fernstrom (57) ABSTRACT

An educational tool for building healthy minds and strong bodies for a healthier generation, built upon the legacy of healthy living represented by a Lunch Box lifestyle. A board game and method for playing the board game which incorporates various healthy lifestyle learning lessons with exercises as part of an activity that is engaged in for enjoyment, health and nutritional education, exercise and fitness, entertainment and fun, for the purpose of bringing health and fitness back to the forefront of children's daily lives. Some embodiments provide the structure of the game, namely, the board and playing pieces, the several different playing cards, dice and their collective interaction, and the method of playing the game in combination with exercises whereby healthy lifestyle choices are learned and physical fitness is enhanced. The game can be played by 2-4 individuals or by 2-4 teams each made up of any number of individuals.

8 Claims, 6 Drawing Sheets

(56) References Cited

U.S. PATENT DOCUMENTS

| | | |
|---|---|---|
| 7,896,347 B1 | 3/2011 | Vail |
| 8,052,149 B2 | 11/2011 | Sweeting |
| 8,087,994 B2 | 1/2012 | Englman et al. |
| 8,091,893 B2 | 1/2012 | Whitaker |
| 8,100,757 B2 | 1/2012 | Melendez |
| 8,104,768 B2 | 1/2012 | Al-Buijan |
| 8,454,367 B2 * | 6/2013 | Roberts .......................... 434/129 |
| 2007/0222147 A1 * | 9/2007 | Blaha et al. ................ 273/149 R |
| 2007/0269773 A1 * | 11/2007 | Slade .............................. 434/98 |
| 2008/0197570 A1 * | 8/2008 | Lewis et al. ................... 273/292 |

* cited by examiner

LUNCH BOX BOARD GAME

CROSS-REFERENCE TO RELATED APPLICATION

This U.S. Utility Patent Application claims priority based upon the previously filed U.S. Provisional Patent Application No. 61/442,446, titled "Lunch Box Board Game," filed on Feb. 14, 2011, the entire disclosure of which is hereby incorporated herein by this express reference.

FIELD OF THE INVENTION

The present invention generally relates to a board game and a method for playing the board game as part of a body and brain challenging activity. More particularly, the present invention relates to a board game and a method for playing the board game which combines lessons on a healthy lifestyle with physical exercise as part of an activity that is engaged in for enjoyment, health and nutritional education, exercise and fitness, entertainment and fun.

BACKGROUND

Physical fitness plays an important role in developing and maintaining a healthy mind and body. Moreover, the interrelatedness of good nutrition and exercise habits and a healthy cardiovascular system has been well documented.

According to the Center for Disease Control and Prevention, over the past three decades childhood obesity rates have doubled for preschoolers aged 2-5 years and teens aged 12-19 and have tripled for children aged 6-11 years. There has been a corresponding and steady increase in obesity-related diseases.

Keeping kids and families engaged through physical activity is a key essential for leading happier and healthier lives. Providing teachers with an "in-school" activity that can include an entire classroom in an interactive learning, fun and physically challenging experience is imperative as schools have been moving physical activity out of the school due to budget cuts, time constraints and an emphasis on testing.

Propelled by consumer demand and initiatives such as Michelle Obama's "Let's Move!" campaign, toy and game makers have stepped up their efforts to develop toys and games that offer active solutions for the whole family. When products are engaging and fun, kids of all ages will stick with them longer, thereby deriving greater health benefits.

"Active Play" toys and games, which were identified as one of the four top toy trends spotted during Toy Fair 2010, can serve as a catalyst for both the body and the brain. "Active Play" toys and games, i.e., those that emphasize a physical (exercise) component, are the obvious way to get kids up and moving, keep the body active, limber and flexible, and promote healthy lifestyle choices. The outdoor games segment is flourishing with game and outdoor sports play for kid and family activities. Exemplary products include Hasbro's Nerf and Super Soaker blasters, Playskool Games' Pop Goes Froggio, Mattel's Red Rover Mattel, Haywire Games' Flickin Chicken, and Diggin Active's Squap. Even indoor products that have a high-tech component such as the Wii and SWINX gaming systems are designed to foster "kid-generated action" by incorporating movement into the game . . . think "kid=remote". Other examples, such as Wild Planet's Hyper Dash Extreme and Sonic Slam by Radica capitalize on a programmed degree of randomness to combine thinking and movement.

"Active imagination and intelligence" toys and games can also promote health and well-being. The Alzheimer's Association recommends puzzles as therapy because some studies have suggested they might improve memory, attention and problem solving while staving off mental decline and, perhaps, reducing the risk of Alzheimer's disease. Paul D. Nussbaum, a clinical neuropsychologist and an adjunct professor of Neurological Surgery at the University of Pittsburgh, School of Medicine, believes that taking better care of your brain can solve mental lapses and forgetfulness, and reduce stress. A brain-healthy lifestyle can do for the brain what a heart-healthy lifestyle has done for the heart, says Nussbaum. Focusing on "Play with a Purpose," active imagination and active intelligence toys and games stimulate the mind and creativity through hands-on play experiences. Examples within this category range from brain teasers and "creativity generators" such as logic games and puzzles to role-play and dress-up items. All inspire pure imaginative play through hands-on, personal experiences with the products. Building sets, arts and crafts and thoughtfully selected games and puzzles can improve hand-eye coordination and brain functioning, as well as promote self-esteem with a complete start-to-finish experience. Brain teasers and problem-solving toys, games and puzzles incorporate strategic play scenarios, cooperative teamwork or competitive play scenarios. Many of this year's imagination-centric products empower child-sized role play with dolls and action figures; others encourage kids to create things their own way through engaging arts and crafts and science/discovery experimentations. Many games offer dual play rules, providing both cooperative and competitive play rules in the instructions to allow for different play scenarios with the same purchase. The intergenerational influence is also a key component in this area of active play, with many family-friendly options to keep the whole family engaged and connected.

Kids' games and toys that are currently emerging have a focus on several key drivers: (i) social development; (ii) affordability; (iii) performance play; and (iv) brain challenging activities.

Kids are becoming ever more engaged with their playmates and their own dreams and ambitions as "Simply Social" toys and games flood retail outlets. This exciting new trend includes e-connected toys, cooperative game rules and enthralling, pro-social play products. Lots of social network apps are based on classic toys, but now an increasing number of physical toys are being introduced that originated with or will work with apps. This sub-trend includes virtual worlds and games and toys that have an online component. Social Face-to-Face games that reduce the "wait time" while other players take their turn, "all-play" games that engage each competitor throughout the gaming experience with consensus play, team play games, and cooperative play games are in demand. Games that help to make kids socially aware and to integrate a pro-social play pattern are sought, as are games and toys that teach kids about the world around them and how to be a better citizen (think: eco-friendly, charity, values and manners and about other languages and cultures).

While available data indicates that parents have begun loosening their purse strings a bit following the recession, affordability and the "pennies-per-play" model are still a major priority for parents when shopping for toys. This has meant an expansion of affordable collectible items for boys and girls; "mini" toys (i.e., smaller versions of products already on the market) at "mini" price points; and broadened product lines with toys for every wallet size. This trend also includes games that are constructible, meaning they allow kids to build and re-build their games, creating a new play experience each time.

The "Performance Play" trend capitalizes on a mounting desire among parents, healthcare officials and the government to get kids up and moving to counteract childhood obesity. It also includes play that "exercises" the brain.

Brain-challenging toys and games that encourage logical thinking, strategy and mind puzzles are very much in vogue.

While there are various games that can be played by families and among groups of people, even entire classrooms of children, there still remains a need for a game that incorporates various healthy lifestyle learning lessons with exercises as part of an activity that is engaged in for enjoyment, health and nutritional education, exercise and fitness, entertainment and fun.

It is an object of the present invention to provide a game that uniquely combines an active imagination and intelligence game with an active physical play game, and thus serves as a catalyst for both the brain and the body.

It is a further object of the present invention to provide a game that makes learning "cool" and at the same time is fun and fast paced, satisfying even the most active kid's "need for speed."

It is a still further object of the present invention to provide a game that meets the increasing demands of parents, the government and healthcare officials who are striving to "amp up" educational and active play to ensure a brighter, healthier future for today's kids.

SUMMARY OF THE INVENTION

Disclosed herein is a board game whereby various healthy lifestyle learning lessons are combined with exercises as part of an activity that can be played by 2-4 individual players or by 2-4 teams of any number of individual players.

A first embodiment of the game in accordance with this invention comprises: (i) a board game that features a school with a classic "school population" and both school-related activities and physical exercises; (ii) "Lunch Box" play pieces, each representing one of the individuals or the teams who play the game—acting in the role of students; (iii) "Pop Quiz" cards that contain questions in connection with issues that are selected to be interesting to the players or team members while at the same time also informative, drawn from one or more subject areas, e.g., Science Lab, Library, Cafeteria and Cool Facts; (iv) "Hall Pass" cards that reward the players or teams for actions recognized as being "desirable"; (v) "Snack" cards that reward or penalize individuals or teams depending upon the healthy or unhealthy nature of the snack depicted; and (vi) "Healthy Golden Lunch" tickets that are awarded to players or teams for correctly answering "Pop Quiz" questions, for amassing "Hall Pass" cards or healthy "Snack" cards, or for landing on premium spaces.

More specifically, the game includes 17 unique and funny characters typically found in a school setting, food dice, snack cards, hall passes, 400 educational health and fitness Pop Quiz Questions, Healthy Golden Lunch Tickets, Rules and strategy of the game play with exercise challenges.

The content and complexity of the "Pop Quiz" questions, as well as the level of effort required by the physical exercises, can be varied so that games can be produced in accordance with this invention that can be targeted to different individuals or teams of different ages and skill sets without departing from the teachings and scope of this invention.

In accordance with the present invention, there is also provided a method for playing a board game with two or more individual participants or two or more teams of any number of individuals per team, comprising the steps of:

1. Providing a game board with a multiple of spaces arranged about the board, running in a never-ending loop, with a starting point for each individual or team and a finishing point for each individual or team;
2. Providing each individual or each team with a "Lunch Box" game piece which represents their presence in the game on the game board;
3. Providing a pair of dice with healthy food symbols depicting the numbers on each dice;
4. Having the first player roll the two dice and begin to move his or their "Lunch Box" game piece around the board;
5. Having the first player take the action required of him or them based upon the space landed upon—including in any exercise activity specified, individually if playing alone or collectively as a group if playing as a team;
6. Having the first player draw a Pop Quiz card of the select type if called for by the space landed upon—and seeing if the first player (individually or collectively as a team) can correctly answer the quiz;
7. Having the first player draw a Hall Pass card if called for by the space landed upon;
8. Having the first player draw a Snack Card if called for by the space landed upon—and seeing if the card is a healthy snack such that the first player receives a reward or is an unhealthy snack such that the first player is penalized;
9. Awarding the first player a Healthy Golden Lunch ticket if called for by the space landed upon, or requiring the first player to give back a Healthy Golden Lunch ticket;
10. Continuing play by having the second and subsequent players or teams roll the dice and similarly move, until one player collects a five (or any other preset number of) Healthy Golden Lunch tickets and returns to their front yard with the five Healthy Golden Lunch tickets in their possession.

DETAILED DESCRIPTION OF THE PREFERRED EMBODIMENTS OF THE INVENTION

In accordance with the present invention there is provided a board game incorporating a plurality of healthy lifestyle lessons and physical exercise as part of game play.

The present invention is easy to learn and can be played by any number of participants, thereby making it ideal for either the privacy of a home, or for the whirling dervish of commotion which is the sine qua non of today's "discipline free" educational institutions, i.e., classrooms.

Figure 1:
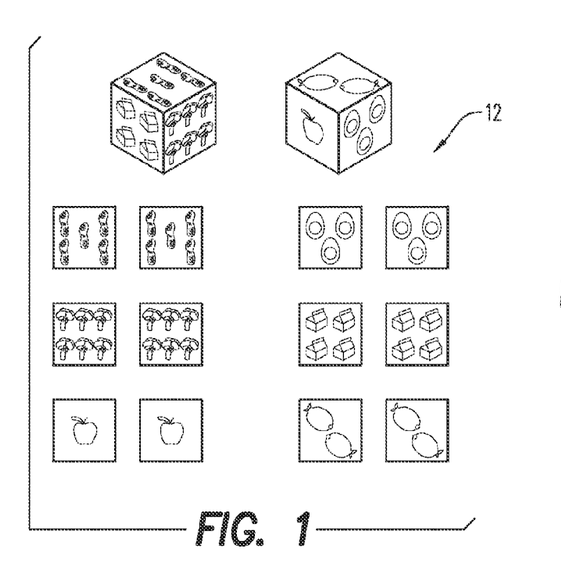
FIG. 1 is a plan view of the six sides of a die of this invention.
Figure 2:
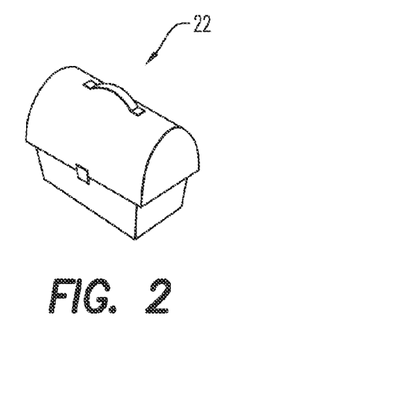
FIG. 2 is a perspective view of a "Lunch Box" playing piece of this invention.
Figure 3A:
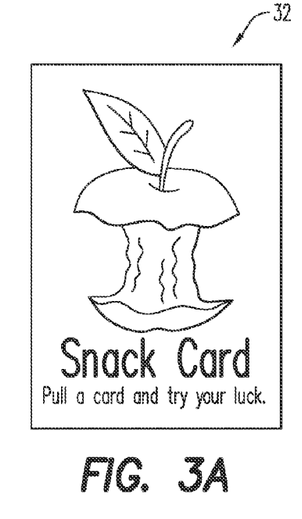
FIGS. 3A, 3B and 3C are top plan views of a front side and two exemplary back sides of Snack Cards of this invention.
Figure 3B:
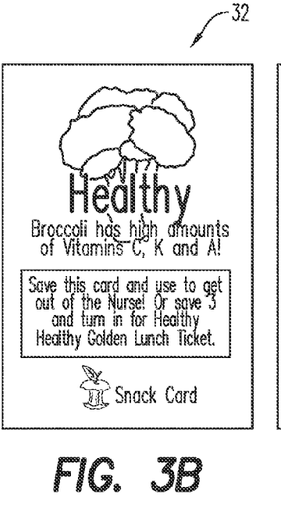
Figure 3C:
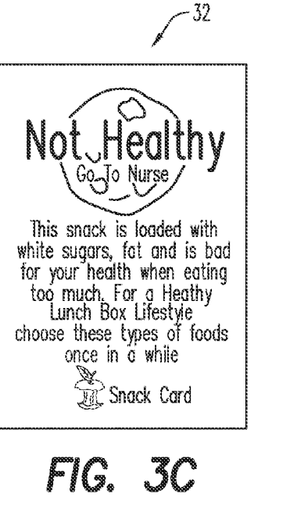
Figure 4:
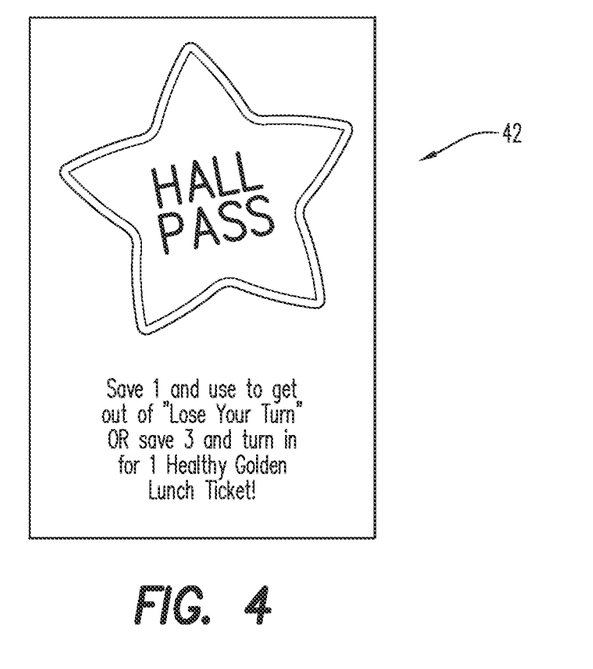
FIG. 4 is a top plan view of a Hall Pass Card of this invention.
Figure 5:
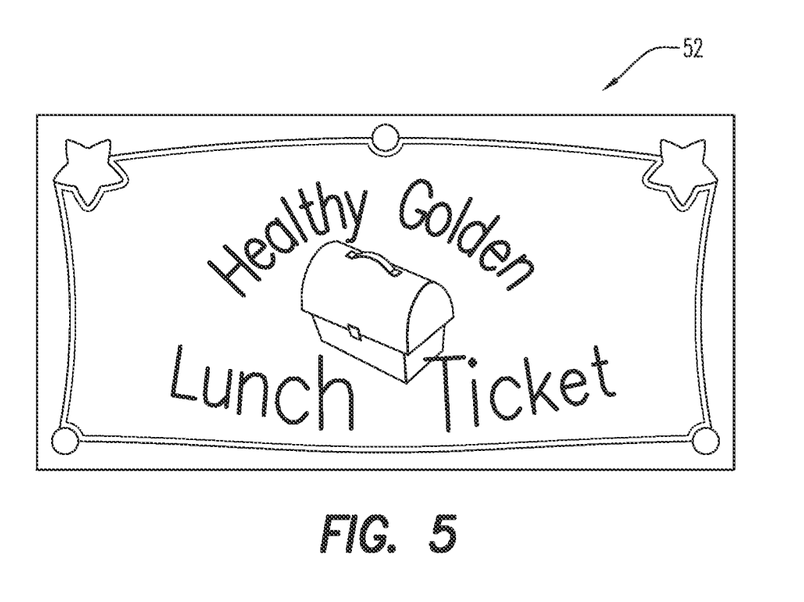
FIG. 5 is a top plan view of a Healthy Golden Lunch ticket of this invention.
Figure 6A:
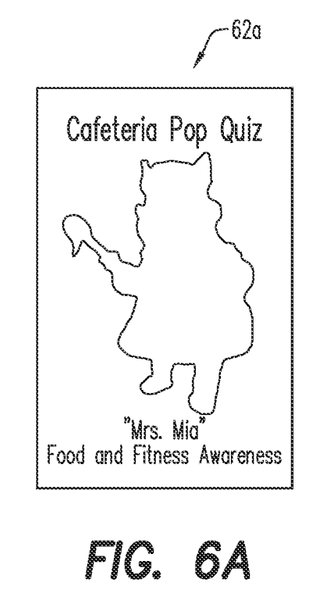
FIGS. 6A, 6B, 6C and 6D are top plan views of the front sides of Pop Quiz cards of this invention.
Figure 6B:
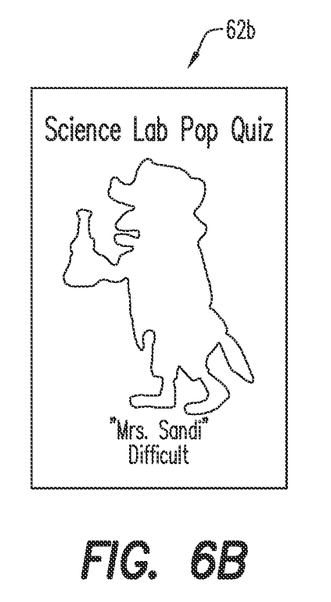
Figure 6C:
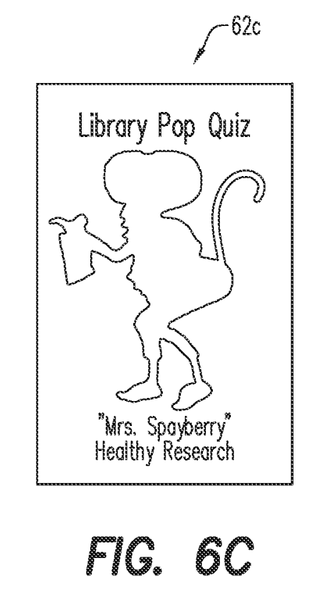
Figure 6D:
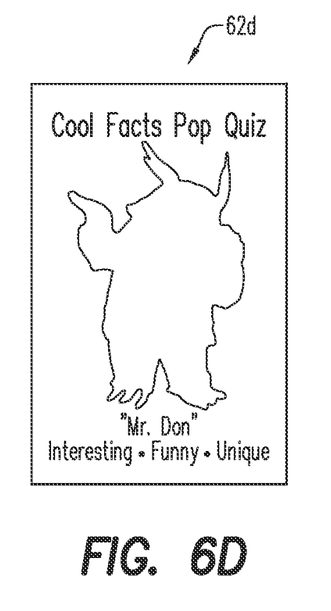
Figures 7A, 7B, 7C, 7D, 7E, 7F, 7G, 7H, 7I:
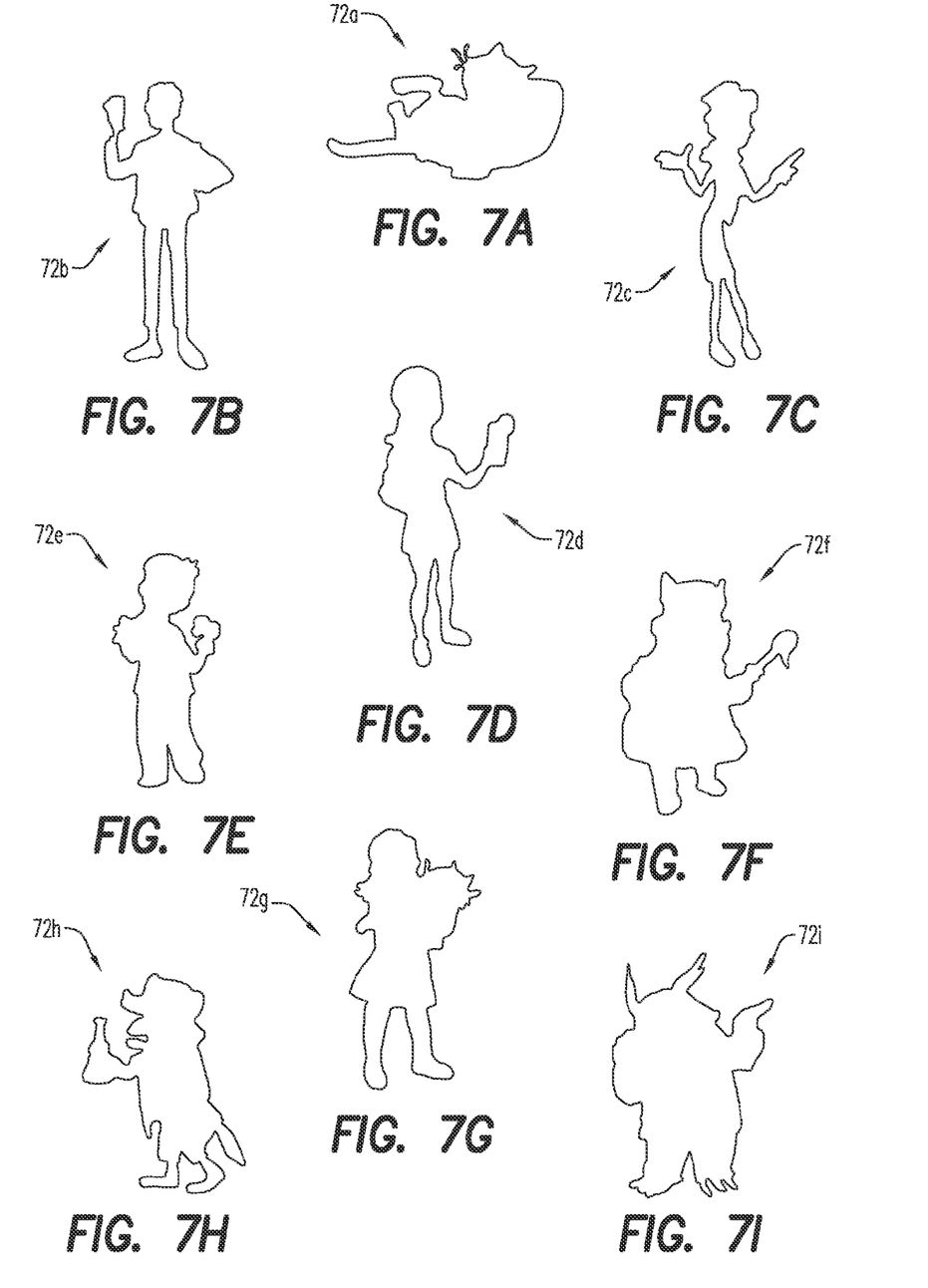
FIGS. 7A-7I illustrate various characters of the game of this invention.
Figure 7J:
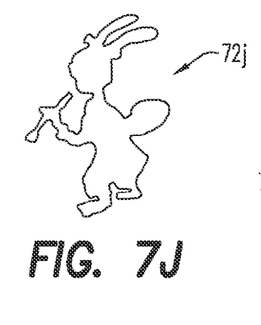
FIGS. 7J-7Q illustrate various other characters of the game of this invention.
Figure 7K:
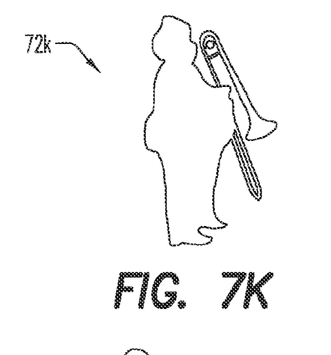
Figure 7L:
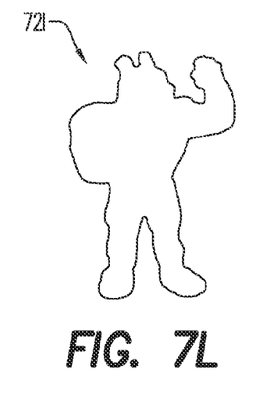
Figure 7M:
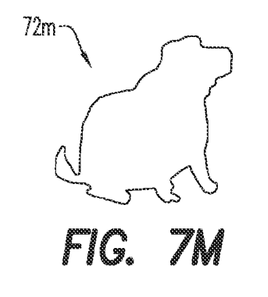
Figure 7N:
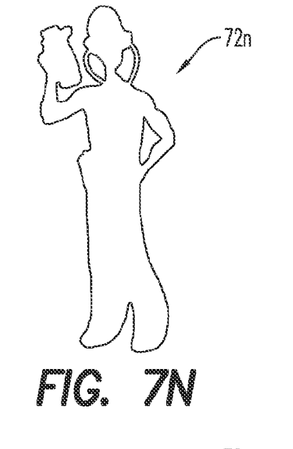
Figure 7O:
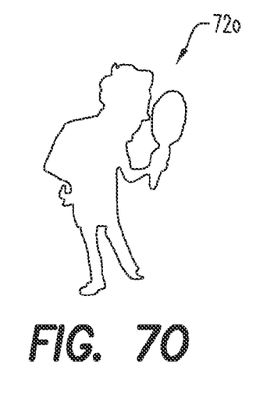
Figure 7P:
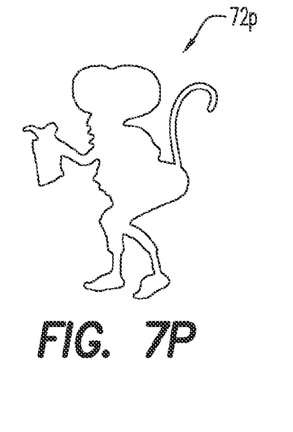
Figure 7Q:
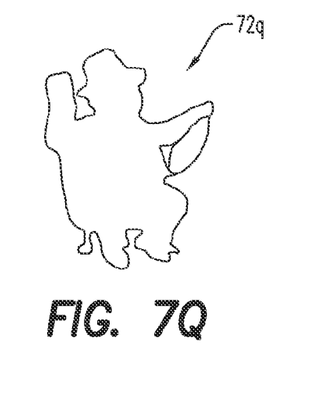
Figure 8:
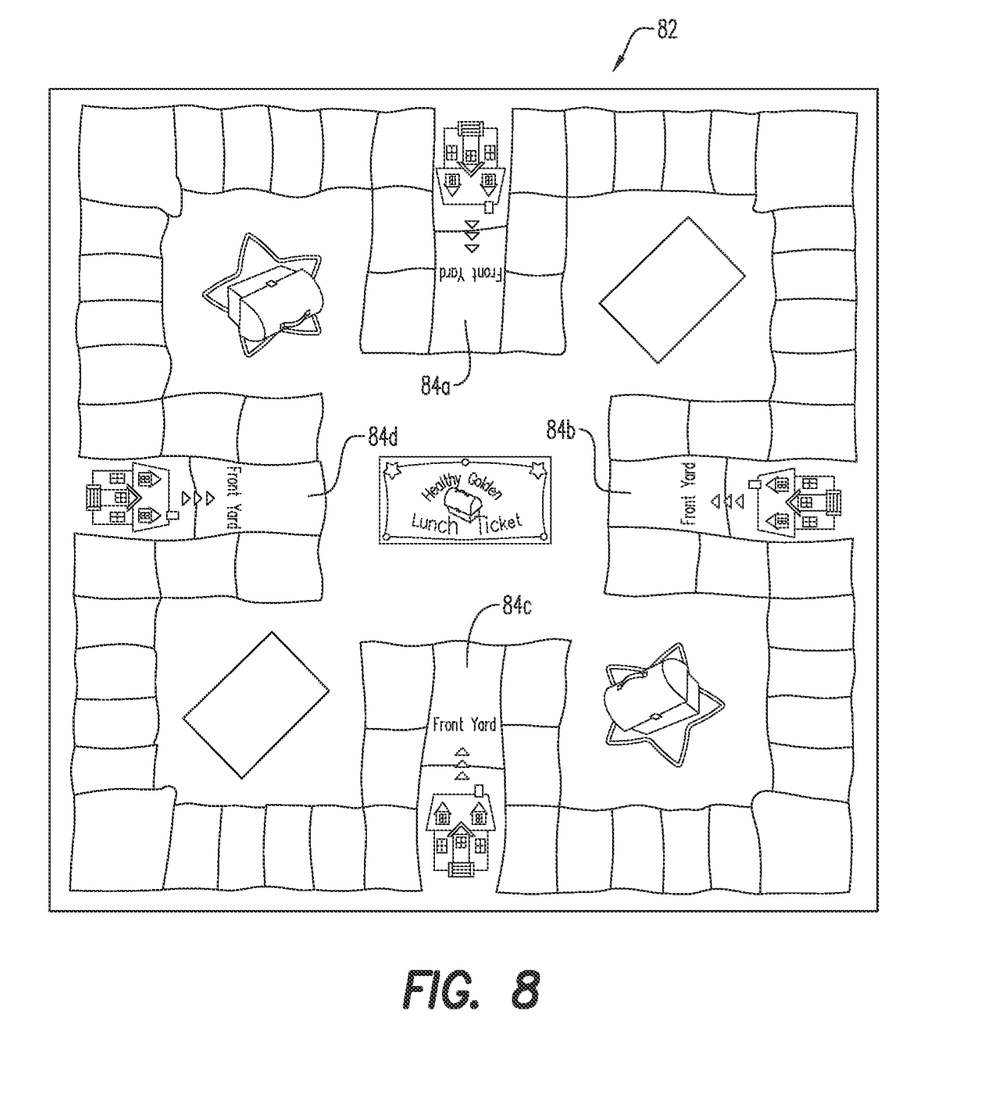
FIG. 8 is a top plan view of the playing board of the game apparatus of this invention.

In the preferred embodiment, the game consists of two dice, one of which 12 is shown in FIG. 1, four "Lunch Box" game pieces of different colors, one of which 22 is shown in FIG. 2, a deck of "Snack" cards 32 shown in FIGS. 3A-3C, a deck of "Hall Pass" cards 42 shown in FIG. 4, a deck of "Healthy Golden Lunch" ticket cards 52 shown in FIG. 5, four decks of "Pop Quiz" cards 62a-62d shown in FIGS. 6A-6D, seventeen characters 72A-72q shown in FIGS. 7A-7Q, and a playing board 82 shown in FIG. 8.

The playing board 82 has four "Front Yards" or starting and finishing points (84a, 84b, 84c and 84d) for up to four individual players or up to four teams of players with any number on each team. The Front Yards are interspersed amongst various contiguous spaces that call upon the player to undertake a particular directive when the player lands on the space.

The order of progression of the spaces, starting with the Yellow Front Yard space, is as follows:
Game Board Progression of Spaces in Preferred Embodiment:

Yellow Front Yard!—Exercise
Snack Card Awarded
Cafeteria Pop Quiz
Junkfood Girl—Advance to Nurse—Exercise
You Have Sugar Bugs in your teeth—Loose your Turn
Science Lab Pop Quiz
Way to go—Hall Pass Awarded
Cool Facts Pop Quiz
Principal's Office—Give Back 1 Healthy Golden Lunch Ticket
H2O—Healthy Golden Lunch Ticket Awarded
Library Pop Quiz
Go Green—Roll Again
Field Trip Yeah!—Stay Here
Way To Go—Hall Pass Awarded
Science Lab Pop Quiz
Sugar Crash—Go to Couch Potato—Exercise
Green Front Yard!—Exercise
Snack Card Awarded
Missed Bus—Go Back Home—Exercise
Way to go—Hall Pass Awarded
Oops . . . caught cheating on a test—Go to Principal's Office—Give Back 1 Healthy Golden Lunch Ticket
Roofus ate your homework!—Go to Study Hall—Loose your Turn
Music Class—Forgot to Practice—Move Back 5 Spaces—Get Snack Card
Cafeteria Pop Quiz
Couch Potato—Exercise
Cool Facts Pop Quiz
Science Lab Pop Quiz
Art Class—Roll Again
Donate canned goods for school fundraiser—Advance 10 Spaces—Get Snack Card
Way to go!—Hall Pass Awarded
Study Hall—Loose Your Turn
Low Blood Sugar Crash—Go to Sleeping in Class—Go to Principal's Office—Give Back 1 Healthy Golden Lunch Ticket
Blue Front Yard!—Exercise
Go Green—Roll Again
Cafeteria Pop Quiz
Oh no . . . you woke up late!—Move Back 3 spaces—Blue Front Yard—Exercise
Junk Food Boy—Advance to Nurse—Exercise
Library Pop Quiz
Snack Card Awarded
Recess . . . Yeah!—Exercise
School Nurse—Exercise
H2O—Healthy Golden Lunch Ticket Awarded
Way To Go.—Hall Pass Awarded
Overslept—Loose Your Turn
Snack Card Awarded
Roofus Ate Your Homework!—Go to Study Hall—Loose Your Turn
Library Pop Quiz
Sugar Crash!—Go to Couch Potato—Exercise
Red Front Yard!—Exercise
Missed Bus—Go Back Home—Exercise
Way To Go . . . —Roll Again
Science Lab Pop Quiz
Oops . . . got caught sleeping in class—Go to Principal's Office—Give Back 1 Healthy Golden Lunch Ticket
Cool Facts Pop Quiz
Cafeteria Pop Quiz
Recess . . . Yeah!—Exercise
P.E. Good Job—Healthy Golden Lunch Ticket Awarded
Overslept—Loose Your Turn
Library Pop Quiz
Fatty Lunch—Go to Couch Potato—Exercise
Oh No . . . you woke up late!—Move Forward 4 Spaces—Yellow Front Yard-Exercise
Computer Lab—Roll Again
Way To Go . . . —Advance to Art Class—Roll Again
Donate canned goods for school fundraiser. Advance 2 Spaces—Snack Card Awarded Exercises in the Preferred Embodiment The exercises which players are called upon to undertake in the preferred embodiment of the game can be seen on the Workout Chart 132 shown in FIG. 13, and include the following:

Push Ups: When you Land on the Front Yard Space that requires you to complete 6 push-ups, lay on the floor with knees down and hands placed shoulder width apart. Push your body up until your arms are straight, then lower back to the ground and repeat. Remember not to hold your breath!

Jumping Jacks: When you Land on the Front Yard Space that requires you to complete 10 Jumping Jacks, stand straight with feet apart and arms above head palms touching. Jump feet together while you bring your arms down to your sides and repeat!

Frog Jumps: When you Land on the Front Yard Space that requires you to complete 8 Frog Jumps, squat down to the floor with feet apart and put your hands in front of you on the floor. Jump up and raise your hands above your head as your feet leave the ground. Repeat.

Abdominal Crunches: When you Land on the Front Yard Space that requires you to complete 8 abdominal crunches, lay on the floor with lower back pressed into floor. Feet stay on the floor and arms are crossed over your chest. Raise your chest and head off the floor about 3-6 inches and exhale as you raise up. Lower back down to the floor and repeat!

Hold Toes Stretch: When you Land on the Nurse if you don't roll apples you need to stand up and try to touch your toes, holding for 15 counts. Make sure you do not hold your breath and keep the back of your legs straight without locking your knees.

Jog in Place: When you Land on the Couch Potato, if you don't roll lemons you'll need to stand up and jog in place for 20 counts. Standing straight, lift one leg then as it lowers to the ground lift the other leg (just like you are running in place). Remember to breath and keep back straight.

Sequence of Play in the Preferred Embodiment

In playing the game, players move around the board 82 with their Lunch Box game pieces 22. They answer questions on the "Pop Quiz" cards 62a-d from select topic areas, such as: Cafeteria, Library, Science Lab and Cool Facts. When they answer the "Pop Quiz" questions correctly they earn Healthy Golden Lunch tickets 52.

The first player to get 5 Healthy Golden Lunch tickets and make it back to their Front Yard Space Wins the game!

If they get caught sleeping in class from a sugar crash—they go to the Principal's Office and lose a Healthy Golden Lunch Tickets!

If they are not careful, they land on Couch Potato and must roll lemons or jog in place to get out!

They can try their luck pulling a Snack Card but if it is an unhealthy snack then they go to the Nurse and must roll apples or stand up and touch their toes to get out!

If they are lucky they may land on P.E. where they will earn a FREE Healthy Golden Lunch Ticket for all their efforts and improved strength, flexibility and confidence!

But they need to watch out for spaces like "Roofus ate your homework" or "Late for school" as they will lose their turn!

Hopefully they will make the honor roll and earn a FREE Hall Pass, which will get them out of losing their turn.

With so much fun and action, players will almost laugh themselves silly when their opponent lands on their Front Yard Space and must stand up to do the yard's mandatory exercise, namely, Frog Jumps, Push Ups, Jumping Jacks or Abdominal Crunches!

This game is so much fun that no one will even realize that they just learned what a carbohydrate is and which foods are the best choices for living a Healthy Lunch Box Lifestyle!

Or that they just had a vigorous workout!

Characters

To make the Lunch Box game even more fun than it is innately, the game board is populated with various "colorful" people that one might expect to find at a mythical school:

Couch Potato~"Rocky Road"~An overweight, brown cat, with brown spots and white strips. He plays video games, eats his favorite snacks "Fish'in Chips", soda and ice cream all day while he lounges on his favorite old couch! His owner is Lizzy Love aka "Junk Food Girl".

Nurse~"Mrs. Cindy"~A funny, thin woman, with a large nose, red hair, and green crossed-eyes. She is always running around frantic and trying to help everyone!

Principal~"Cap'n Grimes"~A retired Navy Captain who is hard core with the children, always taking their Healthy Golden Lunch tickets away. When he was a little boy he always wanted to be a pirate. Now that he is older he dreams about the Healthy Golden Lunch tickets as being "real gold." He is a bit nerdy and the kids don't really like him all that much. He is tall and can be rather obnoxious—trying to talk like a "pirate all the time." Beneath it all he has a BIG SECRET. He loves Junk FOOD! Always eating his favorite chips, "Commander Cool Chips" the greasiest, saltiest chips around!

P.E Teacher~"Coach Cutt"~A overly happy, pretty, very fit female coach, she has visible muscle definition. She has blonde hair, blue eyes and a "never quit", CAN DO Attitude! She loves teaching the kids about which healthy foods to eat and the proper ways to exercise! She loves to drink her signature, freshly squeezed H2O lemonade!

Junk Food Boy~"Littles Kent"~A slightly chubby, blonde haired boy with outrageous colored clothes. He always wears a fitness headband with USA colors of red, white and blue. He LOVES eating chocolate, and lollipops. He is hyper, loud, and funny. He loves to workout with Coach Cutt but can't seem to eat good healthy foods. He is the class clown and is very popular due to his very friendly nature. His pet is Roofus, the dog, who likes to eat homework!

Junk Food Girl~"Lizzy Love"~A pretty, chubby, blonde haired girl with pigtails and brown eyes. She is always wearing a dress. She loves fried fatty foods and salty movie theater popcorn. She is a straight A student who loves getting the teachers approval. Her pet is "Rocky Road" the cat aka "Couch Potato" who sits on the couch all day!

Cafeteria Cook~"Mrs. Mia"~A plump pig lady with a hair net and large moles on her face. She has brown hair and brown eyes. She loves serving her signature smiley face slop with a "secret ingredient", organic creamed spinach. She is first in line for Coach Cutt's aerobics class, with energy for all!

Science Lab~"Mrs. Sandi"~A hyena who is crazy, but brilliant, and loves teaching kids. She has long eyelashes and bottle glasses that make her eyes pop. Every day she wears a new pair of glasses with colored frames that match her wild multi-colored socks. She wears earrings and lots of lipstick. Her hair is thick, shiny and she is always complimented on how nice it looks!

Cool Facts~"Mr. Don"~A hip owl with groovy, square glasses and a gold medallion necklace with the letters LB for "Live Bold"! He is the most popular teacher, as all the kids love him. His class is the most fun, interesting and exciting at school!

Art Class~"Ms. Daisy Blossom"~A beautiful, white, young bunny lady with bright blue eyes! With her head in the clouds she is always happy and loves glittery things. She is constantly painting, drawing flowers, butterflies and rainbows! She loves the kids and they love her too!

Music Class~"Trombone Bob"~A chubby, jolly man with a heart of music! He is always playing his trombone and is terrible at it but thinks he is the world's best. He has thick gray hair that is greased back and sparkling blue eyes. He loves singing and has a great jolly singing voice. He is always singing the "oldies music". The kids make fun of his terrible trombone playing all the time behind his back. The children do love to hear him sing with his "Elvis Style" voice, but wish he would sing more current hip tunes!

Study Hall Teacher/Assistant P.E. Coach~"Mr. Rockhead"~A large muscular brown bear who wears tank tops everyday. He is a bit scary with his presence. He is always right, at least he thinks so. Constantly preaching and blurting out in a loud roaring voice his point of view on everything and anything. He really has a heart of gold and is very lovable. Mr. Rockhead has a crush on Ms. Cutt, the P.E. teacher, but she doesn't pay him any attention. HE thinks that Coach Cutt is "in love" with him. He is always trying to get her attention by working out with his big muscles, showing off with his strength and charm!

Dog~"Roofus"~A VERY LARGE, OBESE, golden Labrador dog who loves to eat homework, and sleep all day! He is called Roofus as he is so overweight and he needs an overly sized dog house, with a HUGE ROOF! His owner is Littles Kent, aka "Junk Food Boy"!

H2O~"Ben-Jamm-in"~A VERY TALL, lean, popular boy, with black hair and brown eyes. He is always wearing his earphones listening to music. He helps all the kids by making sure they have H20. He is the best at "every sport" in school placing first in everything with ease!

Dentist~"Mr. Gum"~A very healthy man with super white, shiny, star quality teeth. He is very happy, funny and just loves TEETH. He likes children but really loves himself the most as he carries around a small mirror always looking at his smile!

Bus Driver~"Mr. Al"~A middle aged man who is short and squatty, can barely see over the steering wheel. He drives crazy and is always drinking his favorite energy drink "Noodle Doodle". The school bus has HUGE MUD tires and dark tinted windows. The kids love riding to school on his bus, as he is always playing groovy tunes that the kids love to cruise to school with!

Library~"Mrs. Spayberry"~(Babs Baboon Spayberry) A old lady baboon with a large butt. She is always wearing tight high water pants which make her large butt look even bigger. She has old fashioned lace up boots. She is obnoxious with her jumping around putting up books. She is constantly eating salty, chocolate covered chips and bananas. She is always dropping crumbs everywhere. She loves books and children. The kids think she is funny and love to hear her tell stories with her thick New York accent at story time!

Game Play Rules:

Game components: 1 Board Game, 4 Lunch Box game play pieces, 1 set of food dice, 30 "Healthy Golden Lunch" tickets, 40 "Hall Pass" cards, 40 "Snack" cards, 100 Cafeteria "Pop Quiz" Questions, 100 Science Lab "Pop Quiz" Questions, 100 Library "Pop Quiz" Questions, and 100 Cool Facts "Pop Quiz" Questions.

How to set up the game: Open the game board and place it on a flat surface. Shuffle and snack the decks of cards in a place close enough for all players to reach. Each player/team picks a "Lunch Box" game piece and places it on the house that matches the color of their "Lunch Box."

Object: Be the first player/team to collect 5 "Healthy Golden Lunch" tickets and make it back to your front yard space!

Game Time: On average it takes 20-30 minutes to play the game with the winner having 5 "Healthy Golden Lunch" tickets. If players do not have that much time, they can simply assign a lower number of "Healthy Golden Lunch" tickets that must be amassed to win in order to shorten the game time. For example, before starting the game, all opponents could agree to only play until someone amasses three "Healthy Golden Lunch" tickets.

Start Game: Role dice to see who goes first. Highest number goes first. Then everyone else goes, moving about the Board in a clockwise direction. The game can also be played in teams. There can be any number of players on each team.

Roll Doubles on Dice: If you roll doubles on your dice of any number, you have the choice of moving the total number of spaces for both dice OR choose to move just the number of spaces for one dice. Example: You roll 5 peanuts and 5 peanuts. You can move 5 spaces OR choose to move 10 spaces!

Winner: First person to earn 5 "Healthy Golden Lunch" tickets for your Lunch Box and make it back to your Front Yard Space is the WINNER!

Once you get all your lunch tickets, when it is your turn again, you just need to roll the dice and move along to your house.

You do not have to continue playing the game board but you do need to continue the exercises if you land on an opponent's Front Yard Space or Recess! You also need to follow the rules if landing on Principal, Nurse, P.E., and Couch Potato!

If an opponent lands on the same space as you on your way home you will get booted off to Couch Potato.

If you land on Principal and lose one of your Healthy Golden Lunch Tickets then you are no longer on your way home, as you will only have 4 tickets now, and must resume playing the board in hopes to gain another Healthy Golden Lunch Ticket! Once you have 5 Healthy Golden Lunch Tickets you can try again to make it back home to your front yard space to win!

TO WIN you either land on your front yard space or pass your front yard, you do not need to roll the exact number.

Once you win, then the remaining opponents must get up and do the exercise from your front yard space.

NOTE Only one person is allowed to be on a single space at one time, except for P.E., Principal, Nurse and Couch Potato. If you land on the same space as your opponent then your opponent must go to Couch Potato.

Snack Card Pile: Try your luck! Pick a card from the snack card pile, if it is a healthy food you are safe and can hold onto this card, as you can use it to get out of Nurse. If your snack card is an unhealthy snack, return Snack Card to bottom of Snack Card Deck and then you must go to the Nurse! Note: You can save up 3 Healthy Snack Cards and trade them in for 1 Healthy Golden Lunch Ticket.

Some of the other directives as you make your way around the board:

Junk Food Boy~"Littles Kent": Ate too much junk food—go to Nurse!

Junk Food Girl~"Lizzy Love": Ate too much junk food—go to Nurse!

Couch Potato~"Rocky Road": You must roll 2 or 4 lemons to get out! If you do not roll lemons then you must stand up and jog in place while EVERYONE counts out loud to 20, then move the number of spaces of your roll.

HALL PASS: Turn in your HALL PASS to get out of losing your turn! OR save up 3 Hall Passes and turn in for 1 Healthy Golden Lunch Ticket!

Study Hall "Mr. Rockhead": Lose your turn!

Dentist "Mr. Gum": Went to the dentist and you have sugar bugs in your teeth! Lose your turn!

LOSE YOUR TURN: You can use a Hall Pass to get out of lose your turn. If you are on a space that says you lose your turn and an opponent lands there, you will get booted off and must go to Couch Potato. When your roll comes around again, follow the rules of Couch Potato.

Roofus Ate Your Homework: Go to Study Hall

Field Trip: Your safe . . . enjoy yourself and have fun!

Bus Driver "Mr. Al": Missed bus go back home!

Go Green Roll Again

Recess Time: When any player lands on this space then EVERY player must stand up and do the "group" exercise. Hop on one leg for 10 counts.

Front Yard Space: If you have landed on your opponent's front yard space then you & your team from your house must get up and do the requested exercise while EVERYONE counts. If it is your own front yard then you do not have to do the exercise. Note: If there is no player for that yard space playing the game . . . you still must get up and do the exercise.

Nurse~"Mrs. Cindy": Roll AN apple/s to get out. If you do not roll an apple/s, you need to stand up and touch your toes, holding them while EVERYONE counts out loud to 15, then move the number of spaces from your roll.

NOTE: If you have a healthy snack card you may use this card to turn in and get out of Nurse without having to roll apples or doing the exercise to get out!

NOTE: OR you can save up 3 Healthy Snack Cards and turn them in for 1 "Healthy Golden Lunch" ticket!

Sleeping in Class: Go to principal's office, then follow rules for principal's office.

Principal Office~"Mr. Stanley": Once it is your turn again you must give one Healthy Golden Lunch Ticket BACK to get out! If you do not have any Healthy Golden Lunch Tickets, go to Couch Potato and follow the rules for Couch Potato.

Science Lab~"Mrs. Sandy": These questions are a little more difficult. Get it right and earn a Healthy Golden Lunch Ticket. If you answer incorrectly then you do not receive a Healthy Golden Lunch Ticket.

Cafeteria~Mrs. Mia": These questions are more about foods. Get it right and earn a Healthy Golden Lunch Ticket. If you answer incorrectly then you do not receive a Healthy Golden Lunch Ticket.

Cool Facts~"Mr. Don": These questions are interesting, funny, and unique. Get it right and earn a Healthy Golden Lunch Ticket. If you answer incorrectly then you do not receive a Healthy Golden Lunch Ticket.

Library~Mrs. Spayberry": These questions can be over any subject about health and fitness . . . like if you were in a library researching information. Get it right and earn a Healthy Golden Lunch Ticket. If you answer incorrectly then you do not receive a Healthy Golden Lunch Ticket.

Art Class~Ms. Daisy Blossom: Roll Again

Music Class~"Mr. Bob Trombone": Forgot to practice move back 5 spaces

P.E.~"Coach Cutt": Great job, increase your strength, flexibility and confidence. Earn one FREE Healthy Golden Lunch Ticket.

Water Boy "Ben-Jamm-In": Great job you are re-hydrating yourself with WATER! Earn one FREE Healthy Golden Lunch Ticket.

Healthy Golden Lunch Ticket: How to get a Healthy Golden Lunch Ticket:

Answer a Pop Quiz Question correctly.

Pull a Snack Card that has the "Water Boy Ben-Jamm-In" on it.

Land on the board space P.E.~"Coach Cutt"

Land on the board space with "Water Boy Ben-Jamm-In" on it.

Save up 3 Hall Passes and turn in for 1 Healthy Golden Lunch Ticket.

Save up 3 Healthy Snack Cards and turn in for 1 Healthy Golden Lunch Ticket.

TO WIN THE GAME you must be the first player/team to earn 5 Healthy Golden Lunch Tickets and make it back to your FRONT YARD SPACE!

It should be appreciated that the present invention is not limited to the exact device and instrumentalities and/or to the exact manner of play described herein. Additional embodiments of the present invention will now be apparent to those skilled in the art. Various modifications can be made in the structure of the game apparatus itself and in the steps undertaken in connection with playing the game, including playing by different rules than those set forth above, while nevertheless still remaining within the spirit and scope of the present invention which is defined by the claims set forth below.

What is claimed is:

1. A game apparatus which incorporates various healthy lifestyle learning lessons with exercises as part of an activity that is engaged in for enjoyment, health and nutritional education, exercise and fitness, entertainment and fun, comprising:
   (i) a playing board having a plurality of continuous playing spaces disposed thereon defining a playing path, said playing path having player directives marked thereon;
   (ii) game pieces used to mark the progress of players on said playing board;
   (iii) chance means for determining the number of spaces a player can advance said game piece along said path during the player's turn;
   (iv) at least one deck of "Pop Quiz" cards having printed thereon questions in connection with issues that are selected to be interesting to the players while at the same time also informative;
   (v) a deck of "Healthy Golden Lunch" ticket cards;
   (vi) said player directives including:
      a. directions to engage in a physical exercise;
      b. directions to select one of said "Pop Quiz" cards and to answer the question on said "Pop Quiz" card; and
      c. directions to receive or give back one of said "Healthy Golden Lunch" tickets; and
   (vii) said players also receiving said "Healthy Golden Lunch" ticket cards for correctly answering said "Pop Quiz" questions.

2. The apparatus of claim 1 wherein the difficulty of said "Pop Quiz" questions and the difficulty of said directions to engage in physical exercise are based upon the capabilities of the target players.

3. The apparatus of claim 2, wherein said "Pop Quiz" questions are drawn from the following subject areas: (1) Science, (2) Library, (3) Cafeteria, and (4) Cool Facts; and said physical exercise directions are drawn from the following activities: (a) push-ups; (b) jumping jacks; (c) frog jumps; (d) abdominal crunches; (e) hold toes stretch; and (f) jog in place.

4. The apparatus of claim 1, wherein said chance means comprises at least one die with the numeric values being represented by representations of healthy foods.

5. The apparatus of claim 1, further including:
   (i) a deck of "Snack" cards having printed thereon healthy and unhealthy facts;
   (ii) said player directives further including directions to select one of said "Snack" cards, said "Snack" cards rewarding or penalizing players depending upon the healthy or unhealthy nature of the snack depicted; and
   (iii) said players also receiving said "Healthy Golden Lunch" ticket cards for amassing a certain number of said healthy "Snack" cards.

6. The apparatus of claim 1, further including:
   (i) a deck of "Hall Pass" cards;
   (ii) said player directives including directions to select one of said "Hall Pass" cards, said "Hall Pass" cards rewarding players for actions recognized as being "desirable"; and
   (iii) said players also receiving said "Healthy Golden Lunch" ticket cards for amassing a certain number of said "Hall Pass" cards.

7. A game apparatus which incorporates various healthy lifestyle learning lessons with exercises as a part of an activity that is engaged in for enjoyment, health and nutritional education, exercise and fitness, entertainment and fun, comprising:
   (iv) a playing board having a plurality of continuous playing spaces disposed thereon defining a playing path, said playing path having player directives marked thereon;
   (v) game pieces used to mark the progress of players on said playing board;
   (vi) chance means for determining the number of spaces a player can advance said game piece along said path during the player's turn;
   (vii) a deck of "Pop Quiz" cards having printed thereon questions in connection with issues that are selected to be interesting to the players while at the same time also informative;
   (viii) a deck of "Hall Pass" cards;
   (ix) a deck of "Snack" cards having printed thereon healthy and unhealthy facts;

(x) a deck of "Healthy Golden Lunch" ticket cards
(xi) said player directives including:
   a. directions to engage in a physical exercise;
   b. directions to select one of said "Pop Quiz" cards and to answer the question on said "Pop Quiz" card;
   c. directions to select one of said "Hall Pass" cards, said "Hall Pass" cards rewarding players for actions recognized as being "desirable";
   d. directions to select one of said "Snack" cards, said "Snack" cards rewarding or penalizing players depending upon the healthy or unhealthy nature of the snack depicted; and
   e. directions to receive or give back one of said "Healthy Golden Lunch" tickets; and
(xii) said players also receiving said "Healthy Golden Lunch" ticket cards for correctly answering said "Pop Quiz" questions, for amassing a certain number of said "Hall Pass" cards or said "Snack" cards.

8. The apparatus of claim 7, wherein said "Pop Quiz" questions are drawn from at least one of the following subject areas: (1) Science, (2) Library, (3) Cafeteria and (4) Cool Facts.

\* \* \* \* \*